United States Patent
Carpenter et al.

(10) Patent No.: US 11,512,035 B2
(45) Date of Patent: Nov. 29, 2022

(54) TRANSFER HYDROFORMYLATION FOR THE PRODUCTION OF OXYGENATES

(71) Applicants: Alex Carpenter, Seabrook, TX (US); Andrew Wiersum, Kessel-Lo (BE); Luc Martens, Vlaams Brabant (BE)

(72) Inventors: Alex Carpenter, Seabrook, TX (US); Andrew Wiersum, Kessel-Lo (BE); Luc Martens, Vlaams Brabant (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/275,846

(22) PCT Filed: Aug. 20, 2019

(86) PCT No.: PCT/EP2019/072222
§ 371 (c)(1),
(2) Date: Mar. 12, 2021

(87) PCT Pub. No.: WO2020/057878
PCT Pub. Date: Mar. 26, 2020

(65) Prior Publication Data
US 2022/0041537 A1 Feb. 10, 2022

Related U.S. Application Data

(60) Provisional application No. 62/732,295, filed on Sep. 17, 2018.

(30) Foreign Application Priority Data

Oct. 18, 2018 (EP) ..................................... 18201203

(51) Int. Cl.
C07C 45/69 (2006.01)

(52) U.S. Cl.
CPC .................................. *C07C 45/69* (2013.01)

(58) Field of Classification Search
CPC ..................................................... C07C 45/69
See application file for complete search history.

(56) References Cited

U.S. PATENT DOCUMENTS

| 3,880,913 | A | * | 4/1975 | Smith | .................. | C07C 67/297 568/864 |
| 4,272,444 | A | * | 6/1981 | McCombs | ............. | C07J 7/0005 552/532 |
| 10,723,672 | B2 | * | 7/2020 | Bischof | ................ | B01J 31/2295 |

OTHER PUBLICATIONS

Murphy et al. Rh-catalyzed C-C bond cleavage by transfer hydroformylation. Science, vol. 347, issue 6217, 56-60. (Year: 2015).*

* cited by examiner

*Primary Examiner* — Sikarl A Witherspoon
(74) *Attorney, Agent, or Firm* — Exxonmobil Chemical Patents Inc.

(57) ABSTRACT

The present disclosure provides a method for forming oxygenates from olefins which includes hydroformylation of aldehydes as a formyl source alternative to syngas. In at least one embodiment, a hydroformylation process is performed at low-temperature and at or near ambient pressure for the conversion of olefins into aldehydes, thus reducing the formation of by-products such as via double bond or skeletal isomerization of the feedstock; or via further conversion of the formed aldehydes and alcohols. In at least one embodiment, the use of gaseous olefinic products (e.g., ethylene) instead of strained olefins (e.g., norbornene) improves the control equilibria in transfer hydroformylation reactions.

38 Claims, No Drawings

TRANSFER HYDROFORMYLATION FOR THE PRODUCTION OF OXYGENATES

CROSS REFERENCE TO RELATED APPLICATIONS

This application is a National Phase Application claiming priority to PCT Application Serial No. PCT/EP2019/072222 filed Aug. 20, 2019, which claims priority to the U.S. Provisional Application No. 62/732,295, filed Sep. 17, 2018, and European Patent Application No. 18201203.9 which was filed Oct. 18, 2018, the disclosures of which are incorporated by reference herein in their entireties.

FIELD

The present disclosure relates to processes for producing higher oxygenates from higher olefins via the transfer hydroformylation reaction of aldehydes as an alternative to syngas.

BACKGROUND

Hydroformylation (OXO process) is an important industrial process which involves the preparation of oxygenated organic compounds by the reaction of carbon monoxide and hydrogen (a.k.a., syngas, or synthesis gas) with carbon compounds containing olefinic unsaturation. Both linear and branched aldehydes are formed, which are further converted to alcohols, diols, carboxylic acids, amines, acroleins, acetals and aldol condensation products. Hydroformylation products are widely used as raw materials for a variety of bulk and chemicals, mainly for plasticizers (i.e. additives that increase the plasticity or fluidity of materials), detergents as well as in the synthesis of natural products and fragrances. The reaction is performed in the presence of a carbonylation catalyst (e.g., Rhodium (Rh) or Cobalt (Co)) and resulting in the formation of a compound, for example, an aldehyde, which has one more carbon atom in its molecular structure than the starting olefinic feedstock. Rhodium and cobalt are used commercially, rhodium being generally more active than cobalt. For instance, higher alcohols may be produced in the so-called "OXO" process by hydroformylation of commercial $C_2$-$C_{40}$ olefin fractions to an aldehyde-containing oxonation product, which on hydrogenation yields respective $C_3$-$C_{41}$ saturated alcohols. The crude product of the hydroformylation reaction will contain catalysts, aldehydes, alcohols, unreacted feed, syngas and by-products.

Additionally, syngas is produced by gasification of carbon containing fuel to a gaseous product and is a mixture of carbon monoxide, hydrogen and carbon dioxide. This gasification is accomplished by partial oxidation and/or reforming reactions in gasification and reforming units. Syngas is a mixture of carbon monoxide, carbon dioxide and hydrogen which can then be converted into hydrocarbons and oxygenates. Syngas can be produced from many sources, including natural gas, coal, biomass, or virtually any hydrocarbon feedstock, by reaction with steam or oxygen to effect partial oxidation. Syngas is a crucial intermediate resource for production of hydrogen, ammonia, methanol, and synthetic hydrocarbon fuels.

Furthermore, hydroformylation is broadly utilized on an industrial-scale for the manufacture of oxygenates (e.g., aldehydes and alcohols) from olefinic feeds. Traditional reaction conditions often require elevated temperatures and moderate to high syngas ($H_2$/CO) pressures. For example, cobalt-catalyzed systems utilized on branched higher olefins often require pressures in excess of 1000 psi syngas and temperatures at or near 150° C. Even so-called low pressure processes based on phosphine containing rhodium or cobalt catalysts operate at pressures greater than 100 psi syngas. Hence, there is a need in the art for an improved, cost- and energy-effective process to convert olefins to higher oxygenates without the use of syngas. There is further a need to provide a methane/carbon dioxide free alternative to conventional hydroformylation technology.

The Rh-Xantphos catalyzed transfer hydroformylation reaction, discovered by Dong and coworkers, represents a considerable breakthrough in syngas surrogate hydroformylation technology. Key features of their work include the use of a weakly coordinating anion capable of mediating proton transfer along with the use of strained olefins (e.g., norbornene and norbornadiene) as formyl group acceptors. However, strained olefins were selected by Dong and coworkers since the strain energy of bridged, cyclic, hydrocarbons (approximately 24 kcal/mol) is sufficient to drive transfer hydroformylation reactions to completion. Without relief of ring-strain, transfer hydroformylation reactions involving linear aldehydes and olefins were calculated to be approximately thermoneutral and were expected to be challenging to mediate. Thus, there is a need for transfer hydroformylation processes using aldehydes and olefins and accessing the synthesis of higher oxygenates using higher olefins (e.g., 1-hexene) of which the by-products (e.g., ethylene) would be volatile and easily removed.

References of interest include: Wu, L., Liu, Q., Beller, M., Angew. Chem. Int. Ed., 2014, 25, pp. 6310-6320; Fuentes, J. A., Pittaway, R., Clarke, M. L., Chem. Eur. J., 2015, 21, pp. 10645-10649; Pino, P., Piacenti, F., Bianchi, M., Organic Syntheses via Metal Carbonyls; $1^{st}$ ed.; Wiley: New York, 1977, Vol 2; Fristrup, P., Kreis, M., Palmelund, A., Norrby, P., Madsen, R., J. Am. Chem. Soc., 2008, 130, pp. 5206-5215; Morioka, T., Nishizawa, A., Furukawa, T., Tobisu, M., Chatani, N., J. Am. Chem. Soc., 2017, 139, pp. 1416-1419; Changsoo, K., Matsui, Y., Orchin, M., J. Organomet. Chem., 1985, 279, pp. 159-164; Murphey, S. K., Park, J., Cruz F. A., Dong, V. M., Science, 2015, 347, pp. 56-60; Murphey, S. K. "Activating Aldehyde C—H Bonds: Applications to Hydroacylation and Transfer Hydroformylation" PhD Thesis, Department of Chemistry, University of Toronto, 2015; Czeluśniak, I., Szymanska-Buzar T., Kenwright, A., Khosravi, E., Ring Opening Metathesis Polymerization and Related Chemistry, Springer, 2002, pp. 157-161; Luo, X, Bai, R., Liu, S., Shan, C., Chen, C., Lan, Y., J. Org. Chem., 2016, 81, pp. 2320-2326; Franke, R., Selent, D., Borner, A., Chem. Rev., 2012, 112, pp. 5675-5732; Hebrard, F., Kalck, P., Chem. Rev., 2009, 109, pp. 4272-4282; U.S. Pat. No. 8,604,254; US 20140350307; US 20140350307; U.S. Pat. Nos. 9,181,156; 8,604,254; CN 101774912; US 20150064763; U.S. Pat. Nos. 5,214,220; 4,292,198; FR 2275434; U.S. Pat. No. 3,946,082; Suarez, et al., Journal of Molecular Catalysis (1985), 32(2), 191-199; Sanchez-Delgado, et al., Journal of the Chemical Society, Chemical Communications (1983), (8), 444-445; U.S. Pat. Nos. 9,688, 599; 9,492,813; BR 2006004284; U.S. Pat. Nos. 6,049,011; 6,265,619; 5,520,722; Dong et al., Journal of Organometallic Chemistry (2017), 833, 71-79; Applied Catalysis, A: General (2012), 421-422, 161-163; Karaenan, et al., Organic & Biomolecular Chemistry (2004), 2(22), 3379-3384.

SUMMARY

The present disclosure provides a method for forming higher oxygenates from higher olefins which includes utilizing aldehydes as a formyl (CHO) source alternative to syngas, an olefin, and a catalyst. In at least one embodiment, a method includes contacting a $C_3$-$C_{41}$ aldehyde, a $C_2$-$C_{40}$-olefin, and a metal catalyst and obtaining a $C_3$-$C_{41}$ aldehyde product and an alkene.

In at least one embodiment, a method for preparing aldehydes includes contacting a $C_x$ aldehyde, a $C_y$ olefin, and a metal catalyst in a reaction vessel, wherein x is an integer of from 3 to 41 and y is an integer of from 2 to 40. The method includes obtaining a $C_{y+1}$ aldehyde product and a $C_{x-1}$ alkene product.

A $C_3$-$C_{41}$ aldehyde can be represented by formula (I):

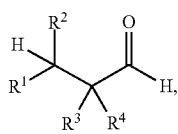
(I)

where each of $R^1$ and $R^2$ is independently hydrogen, alkoxide, or substituted or unsubstituted hydrocarbyl; and each of $R^3$ and $R^4$ is independently hydrogen, or substituted or unsubstituted hydrocarbyl.

A $C_2$-$C_{40}$ olefin can be represented by formula (II):

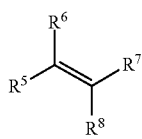
(II)

where each of $R^5$, $R^6$, $R^7$, and $R^8$ is independently hydrogen, or substituted or unsubstituted hydrocarbyl group, such as saturated hydrocarbyl group.

DETAILED DESCRIPTION

The present disclosure provides a method for forming oxygenates from olefins which includes the transfer hydroformylation of aldehydes as a formyl (CHO) source alternative to syngas. The present disclosure further provides transfer hydroformylation processes performed at low-temperature and at or near ambient pressure for the conversion of higher olefins into higher aldehydes, thus reducing the formation of by-products such as via double bond or skeletal isomerization of the feedstock; or via further conversion of the formed aldehydes and alcohols (i.e., formation of condensation products; decarbonylation; further oxidation).

For example, the present disclosure is directed to a transfer hydroformylation process to produce aldehydes, the process including contacting a catalyst system comprising one or more catalysts, and an optional support, with a low cost aldehyde feed and one $C_2$-$C_{40}$ olefin, such as a $C_3$-$C_{18}$ olefin, under mild conditions to afford an aldehyde product and a volatile olefin by-product.

In at least one embodiment, a method utilizes linear alkenes instead of strained olefins (e.g., norbornene) and propionaldehyde (propanal) to control equilibria in transfer hydroformylation reactions by producing gaseous olefinic products (e.g., ethylene) from the propanal starting material. The present disclosure illustrates that transfer hydroformylation is used on olefins having 6 or more carbon atoms, such as 10 or more carbon atoms, and propanal is utilized as a feedstock. In a further embodiment, the present disclosure provides a process for the production of aldehyde mixtures comprising a feed containing one or more aldehyde(s) in a single liquid phase with one or more alkene(s) in the presence of a catalyst comprising a rhodium complex in conjunction with an organophosphorus ligand (such as including a tertiary organophosphine or an organophosphite) and under conditions that completely or partially convert the starting aldehyde(s) to alkene(s) and the starting olefins to a mixture of higher oxygenates. For example, propanal to ethylene and hexene to heptanal.

Methods of the present disclosure provide an attractive alternative to conventional hydroformylation technology by operating under reaction conditions capable of operating at or near ambient pressure with a mild temperature range, typically of 70° C. to 120° C., enabling capital cost savings in new plant construction and operating cost savings for existing hydroformylation units. The present disclosure relates to hydroformylation processes utilizing transfer hydroformylation technology in which a suitable catalyst system (e.g., rhodium phosphine) mediates the apparent transfer of a formyl group from a low-cost aldehyde feed (i.e., propionaldehyde) to a higher olefin in order to produce higher oxygenates (e.g., aldehydes and alcohols) under mild conditions.

Without being bound by theory, in a transfer hydroformylation reaction, a donor aldehyde undergoes a transition-metal mediated decarbonylation reaction to produce a metal carbonyl hydride intermediate. This intermediate can then react with an acceptor olefin to produce the desired hydroformylation product. A notable feature with this chemistry is that the decarbonylation of one aldehyde is efficiently coupled with the hydroformylation of another. Additionally, the removal of the by-products (such as ethylene) facilitates the conversion process of the higher olefins, leading to greater production of the desired higher oxygenates.

The present disclosure provides transfer hydroformylation methods that can provide low-temperature and low pressure processes for the conversion of higher olefins to higher aldehydes. Use of low severity processes reduces the formation of by-products such as double bond or skeletal isomerization of the feedstock; or via further conversion of the formed aldehydes and alcohols (i.e., formation of condensation products; decarbonylation; further oxidation).

Definitions

For the purposes of the present disclosure, the numbering scheme for the Periodic Table Groups is used as described in CHEMICAL AND ENGINEERING NEWS, 63(5), pg. 27 (1985). Therefore, a "group 4 metal" is an element from group 4 of the Periodic Table, e.g., Hf, Ti, or Zr.

In this disclosure, the article "a" or "an" means at least one, unless it is clearly specified or indicated by the context to mean one.

An "isomer" of a first compound is a separate compound in which each molecule contains the same constituent atoms as the first compound, but where the configuration of those atoms in three dimensions differs.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The terms "substituent," "radical," "group," and "moiety" may be used interchangeably.

As used herein, and unless otherwise specified, the term "$C_n$," means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "alkyl group" or "alkyl" interchangeably refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure comprising one or more rings.

The term "aryl group" refers to an unsaturated, cyclic hydrocarbyl group consisting of carbon and hydrogen atoms in which the carbon atoms join to form a conjugated π system. Non-limiting examples of aryl groups include phenyl, 1-naphthyl, 2-naphthyl, 3-naphthyl, and the like.

The term "arylalkyl group" refers to an alkyl group substituted by an aryl group or alkylaryl group. Non-limiting examples of arylalkyl group include benzyl, 2-phenylpropyl, 4-phenylbutyl, 3-(3-methylphenyl)propyl, 3-(p-tolyl)propyl, and the like.

The term "alkylaryl group" refers to an aryl group substituted by an alkyl group. Non-limiting examples of alkylaryl group include 2-methylphenyl, 3-methylphenyl, 4-methylphenyl, 2-methyl-1-naphthyl, 6-phenylhexyl, 5-pentylphenyl, 4-butylphenyl, 4-terterybutylphenyl, 7-phenylheptanyl, 4-octylphenyl, and the like.

The term "cycloalkylalkyl group" refers to an alkyl group substituted by a cycloalkyl group or an alkylcycloalkyl group. An example of cycloalkylalkyl group is cyclohexylmethyl.

The term "alkylcycloalkyl group" refers to a cycloalkyl group substituted by an alkyl group. Non-limiting examples of alkylcycloalkyl group include 2-methylcyclohexyl, 3-methylcyclohexyl, 4-methylcyclohexyl, 4-tertiary butyl cyclohexyl, 4-phenylcyclohexyl, cyclohexylpentyl, and the like.

Substituted hydrocarbyl radicals are radicals in which at least one hydrogen atom has been substituted with a heteroatom or heteroatom containing group, such as with at least one functional group such as halogen (Cl, Br, I, F), $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, or where at least one heteroatom has been inserted within the hydrocarbyl radical, such as halogen (Cl, Br, I, F), O, S, Se, Te, $NR^*$, $PR^*$, $AsR^*$, $SbR^*$, $BR^*$, $SiR^*_2$, $GeR^*_2$, $SnR^*_2$, $PbR^*_2$, where $R^*$ is, independently, hydrogen or a hydrocarbyl.

"Cn" group or compound refers to a group or a compound including carbon atoms at total number thereof of n. Thus, "Cm-Cn" or "Cm to Cn" group or compound refers to a group or compound including carbon atoms at a total number thereof in the range from m to n. Thus, a $C_1$-$C_{50}$ alkyl group refers to an alkyl group including carbon atoms at a total number thereof in the range from 1 to 50.

The term "carbon backbone" in an alkane or an alkyl group refers to the longest straight carbon chain in the molecule of the compound or the group in question.

The term "carbon backbone" of an olefin is defined as the straight carbon chain therein including a C=C functionality having the largest number of carbon atoms.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

An "olefin," alternatively referred to as "alkene," is a linear, branched, or cyclic compound of carbon and hydrogen having at least one double bond.

The term "terminal olefin" refers to an olefin having a terminal carbon-to-carbon double bond in the structure thereof (($R^1R^2$)—C=$CH_2$, where $R^1$ and $R^2$ can be independently hydrogen or any hydrocarbyl group, such as $R^1$ is hydrogen, and $R^2$ is an alkyl group). A "linear terminal olefin" is a terminal olefin defined in this paragraph wherein $R^1$ is hydrogen, and $R^2$ is hydrogen or a linear alkyl group.

The term "vinyl" means an olefin having the following formula:

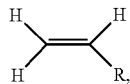

wherein R is a hydrocarbyl group, such as a saturated hydrocarbyl group.

The term "vinylidene" means an olefin having the following formula:

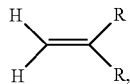

wherein each instance of R is independently a hydrocarbyl group, such as a saturated hydrocarbyl group.

The term "1,2-di-substituted vinylene" means
(i) an olefin having the following formula:

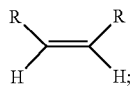

or
(ii) an olefin having the following formula:

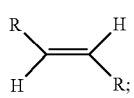

or
(iii) a mixture of (i) and (ii) at any proportion thereof, wherein each instance of R is independently a hydrocarbyl group, such as saturated hydrocarbyl group.

The term "tri-substituted vinylene" means an olefin having the following formula:

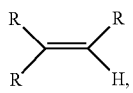

wherein each instance of R is independently a hydrocarbyl group, such as a saturated hydrocarbyl group.

The term "tetra-substituted vinylene" means an olefin having the following formula:

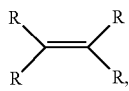

wherein each instance of R is independently a hydrocarbyl group, such as a saturated hydrocarbyl group.

A "substituted alkyl" or "substituted aryl" group is an alkyl or aryl radical made of carbon and hydrogen where at least one hydrogen is replaced by a heteroatom, a heteroatom containing group, or a linear, branched, or cyclic substituted or unsubstituted hydrocarbyl group having 1 to 30 carbon atoms. A heterocyclic ring is a ring having a heteroatom in the ring structure as opposed to a heteroatom substituted ring where a hydrogen on a ring atom is replaced with a heteroatom. For example, tetrahydrofuran (THF) is a heterocyclic ring and 4-N,N-dimethylamino-phenyl is a heteroatom-substituted ring.

The term "heteroaryl" means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

The term "alkoxy" or "alkoxide" means an alkyl ether or aryl ether radical wherein the term alkyl is as defined above. Examples of suitable alkyl ether radicals can include methoxy, ethoxy, n-propoxy, iso-propoxy, n-butoxy, iso-butoxy, sec-butoxy, tert-butoxy, phenoxyl, and the like.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The term "ring atom" means an atom that is part of a cyclic ring structure. By this definition, a benzyl group has six ring atoms and tetrahydrofuran has 5 ring atoms.

For purposes of the present disclosure and claims thereto, the term "substituted" means that a hydrogen group has been replaced with a heteroatom, or a heteroatom containing group. For example, a "substituted hydrocarbyl" is a radical made of carbon and hydrogen where at least one hydrogen is replaced by a heteroatom or heteroatom containing group (as described above).

As used herein, Mw is weight average molecular weight, wt % is weight percent, and mol % is mole percent. Unless otherwise noted, all molecular weight units (e.g., Mw) are g/mol.

Certain abbreviations may be used to for the sake of brevity and include but are not limited to: Me is methyl, Ph is phenyl, Et is ethyl, Pr is propyl, iPr is isopropyl, n-Pr is normal propyl, Bu is butyl, cPR is cyclopropyl, iBu is isobutyl, tBu is tertiary butyl, p-tBu is para-tertiary butyl, nBu is normal butyl, sBu is sec-butyl, p-Me is para-methyl, Ph is phenyl, Bn is benzyl (i.e., $CH_2Ph$), COD is cyclooctadiene, THF (also referred to as thf) is tetrahydrofuran, acac is acetylacetone, RT is room temperature (and is 23° C. unless otherwise indicated), tol is toluene, EtOAc is ethyl acetate, and Cy is cyclohexyl, inHg is inch of mercury, psi is pound-force per square inch.

Oxygenates and Processes for Making the Same
General

In at least one embodiment, the present disclosure relates to methods for forming oxygenates from olefins which includes hydroformylation of an olefin and utilizing an aldehyde (as a formyl (CHO) source alternative to syngas). A method can include contacting an aldehyde (such as a $C_3$-$C_{41}$ aldehyde), an olefin (such as a $C_2$-$C_{40}$ olefin), and a metal catalyst and obtaining an aldehyde product (such as a $C_3$-$C_{41}$ aldehyde product) and an alkene product (such as ethylene).

Aldehydes

Any suitable aldehyde may be used in processes of the present disclosure. In at least one embodiment, an aldehyde is a $C_3$-$C_{41}$ aldehyde represented by formula (I):

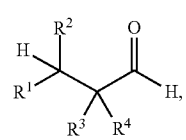

where each of $R^1$ and $R^2$ is independently hydrogen, alkoxide, or substituted or unsubstituted hydrocarbyl, and each of $R^3$ and $R^4$ is independently hydrogen, or substituted or unsubstituted hydrocarbyl. In at least one embodiment, $R^1$ and $R^2$ is hydrogen. $R^3$ and $R^4$ can be independently hydrogen or $C_1$ to $C_{38}$ alkyl, such as $C_1$ to $C_{20}$ alkyl, such as $C_1$ to $C_{10}$ alkyl, such as $C_1$ to $C_5$ alkyl. In at least one embodiment, each of $R^3$ and $R^4$ is hydrogen.

In at least one embodiment, an aldehyde can be one or more of propanal, butanal, pentanal (valeraldehyde), hexanal, heptanal, octanal, nonanal, decanal, undecanal, dodecanal, tridecanal, tetradecanal, pentadecanal, 3-methylbutanal, 3-methylpropanal (isovaleraldehyde), 4-methylpropanal, unsubstituted and substituted cyclohexanecarbaldehyde. Using an aldehyde that will convert into a gaseous olefinic product, such as propanal and ethylene respectively, provides control of the hydroformylation reaction equilibria due to volatility (and easy removal) of the gaseous olefinic product from a reaction vessel. Furthermore, using inexpensive propanal as feedstock on higher olefins leads to the formation of higher oxygenates. Propanal is also a facile starting material to form by hydroformylation of ethylene, and the ethylene as a byproduct of a process of the present disclosure may be recycled to form additional propanal.

In at least one embodiment, a molar ratio of the aldehyde and the olefin is from 20:1 to 1:1, such as from 15:1 to 1:1, such as from 10:1 to 2:1, such as from 5:1 to 2:1.

Olefins

Olefins used in processes of the present disclosure may be alpha-olefins, 1,2-di-substituted vinylenes, or tri-substituted vinylenes.

Any suitable olefin may be used in processes of the present disclosure. In at least one embodiment, an olefin is a $C_2$-$C_{40}$ olefin represented by formula (II):

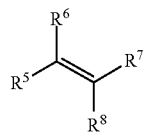

where each of $R^5$, $R^6$, $R^7$, and $R^8$ is independently hydrogen, or substituted or unsubstituted hydrocarbyl group, such as saturated hydrocarbyl group. In at least one embodiment, the olefin is an alpha-olefin where $R^7$ and $R^8$ is hydrogen.

In at least one embodiment, each of $R^5$, $R^6$, and $R^7$ is independently hydrogen, or a substituted or unsubstituted hydrocarbyl group. In at least one embodiment, $R^5$, $R^6$, and $R^7$ are independently hydrogen or $C_1$ to $C_{38}$ alkyl, such as $C_1$ to $C_{20}$ alkyl, such as $C_1$ to $C_{10}$ alkyl, such as $C_1$ to $C_5$ alkyl. In at least one embodiment, one or more of $R^5$, $R^6$, and $R^7$ is $C_1$ to $C_{38}$ alkyl, $C_1$ to $C_{20}$ alkyl, such as $C_1$ to $C_{10}$ alkyl, such as $C_1$ to $C_5$ alkyl.

In at least one embodiment, one or more of $R^5$ and $R^6$ is $C_{10}$ to $C_{38}$ alkyl, such as $C_{20}$ to $C_{38}$ alkyl, such as $C_{30}$ to $C_{38}$ alkyl. In at least one embodiment, $R^5$ is hydrogen and $R^6$ is $C_{10}$ to $C_{38}$ alkyl, such as $C_{20}$ to $C_{38}$ alkyl, such as $C_{30}$ to $C_{38}$ alkyl.

In at least one embodiment, suitable olefins include substituted or unsubstituted $C_2$ to $C_{40}$ olefins, such as $C_2$ to $C_{20}$ olefins, such as $C_2$ to $C_{12}$ olefins, such as ethylene, propylene, butene, pentene, hexene, heptene, octene, nonene, decene, undecene, dodecene and isomers thereof. The $C_2$ to $C_{40}$ olefin monomers may be linear, branched, or cyclic. The $C_2$ to $C_{40}$ cyclic olefins may be strained or unstrained, monocyclic or polycyclic, and may optionally include heteroatoms and/or one or more functional groups.

In at least one embodiment, suitable olefins include $C_2$ to $C_{40}$ olefins, such as $C_2$ to $C_{20}$ olefins, such as $C_2$ to $C_{12}$ olefins, such as ethylene, propylene, butene, pentene, hexene, heptene, octene, nonene, decene, undecene, dodecene. In at least one embodiment, the $C_3$ to $C_{40}$ olefin monomers may be linear and may optionally include heteroatoms and/or one or more functional groups.

A $C_2$ to $C_{40}$ olefin, such as a $C_2$ to $C_{18}$ olefin, can be ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, such as hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective isomers, homologs and derivatives, such as norbornene, norbornadiene, and dicyclopentadiene.

For the purposes of the present disclosure, ethylene shall be considered an alpha-olefin.

In at least one embodiment, the alkene is a gaseous olefin, the olefin pressure in a reaction vessel is greater than about 5 psig (34.5 kPa), such as greater than about 10 psig (68.9 kPa), such as greater than about 45 psig (310 kPa), and the pressure in the reaction vessel is less than 150 psig. When a diluent is used with the gaseous alkene, the aforementioned pressure ranges may also be suitably employed as the total pressure of olefin and diluent. Likewise, when a liquid alkene is employed and the process is conducted under an inert gaseous atmosphere, then the aforementioned pressure ranges may be suitably employed for the inert gas pressure.

Metal Catalyst

A "catalyst system" includes any suitable rhodium precursor, at least one organophosphorous ligand and a suitable carboxylic acid. The catalyst system may be generated by combining the catalyst components suitable fashion to afford an active catalyst complex. The combination of the organophosphorous ligand and a metal precursor can be used to afford an un-activated catalyst complex (pre-catalyst) which may be isolated or generated in situ. When "catalyst system" is used to describe the catalyst compound before activation, it means the metal precursor together with an organophosphorous ligand. When it is used to describe the combination after activation, it means the combination of transition metal precursor/organophosphorous ligand and a carboxylic acid. The transition metal compound may be neutral as in a pre-catalyst, or a charged species. For the purposes of the present disclosure, when catalyst systems are described as including neutral stable forms of the components, it is well understood by one of ordinary skill in the art, that the ionic forms are also accessible. For example, a carboxylate anion may be associated with a transition metal to afford a neutral species or dissociated to afford a transition metal cation and a carboxylate anion.

The catalyst system and/or a component thereof may be oxygen and/or moisture sensitive, and accordingly, its preparation and/or storage and/or use during the hydroformylation process may be carried out substantially in the absence of oxygen and/or moisture. In at least one embodiment of the present disclosure, the preparation of the catalyst and/or the hydroformylation reaction is carried out in an inert atmosphere, for example a nitrogen or helium atmosphere or an argon atmosphere. In at least one embodiment, the preparation of the catalyst and/or the hydroformylation reaction is carried out in an inert gas-filled environment, for example a glove box.

A variety of rhodium pre-cursors and organophosphorous ligands can be can be used in the present disclosure. Hydroformylation reactions of lower olefins such as ethylene, propylene and butenes have generally employed rhodium catalyst stabilized by phosphorus containing ligands operated in what is known as the low pressure Oxo (LPO) technology. The present disclosure provides a process that operates under near to ambient pressure. In another embodiment, cobalt containing catalysts are used and the process is operated at higher pressures. In a similar way to cobalt, also rhodium catalyzed hydroformylation may be operated at higher pressures, and in some embodiments, without a stabilizing ligand other than carbon monoxide or with a weak ligand like e.g., triphenylphosphine oxide (TPPO). The present disclosure provides an Rh- or Co-mediated hydroformylation process that operates under near to ambient pressure.

In the description herein, the catalyst $M[L]_n$ may be described as a catalyst precursor, a pre-catalyst compound, $M[L]_n$ catalyst compound or a transition metal compound, and these terms are used interchangeably (where M is rhodium, L is any suitable ligand, such as phosphine, capable of coordinating a group 9 metal, and n is a positive integer, such as 1, 2, 3, 4, 5, or 6). An "anionic ligand" is a negatively charged ligand which donates one or more pairs of electrons to a metal ion. A "neutral donor ligand" is a neutrally charged ligand which donates one or more pairs of electrons to a metal ion.

A metal catalyst can be represented by formula (III):

$$M[L]_n X \tag{III}$$

Where M is rhodium, L is any suitable ligand, such as phosphine, capable of coordinating a group 9 metal, n is a positive integer, such as 1, 2, 3, 4, 5, or 6, and X is a weakly coordinating anionic ligand, such as an alkyl or aryl carboxylate.

The catalyst contained in the reaction mixture can be any suitable rhodium metal complex with a ligand. It will be understood that, while the complex is characterized as comprising the metal and the organic ligand, the active catalyst as it actually functions is, without being bound by theory, an organophosphorous stabilized metal carboxylate. Ligands can include monodentate or polydentate triorganophosphines, triorganophosphites, triorganoarsines, or triorganostibines, with the phosphines and phosphites being of particular industrial importance. For example, simple monodentate phosphines and phosphites, as exemplified by triphenylphosphine and triphenylphosphite may be used. However, polydentate ligands have advantages in that large excesses of ligand which are often used, unlike when monodentate ligands are used. Carboxylate anions can include but are not limited to aryl carboxylates, such as 3,5-dimethylbenzoate, and alkyl carboxylates such as, stearate or hexanoate or naphthenate.

Any suitable concentration of catalyst can be used in a hydroformylation reaction medium of the present disclosure. For example, when the catalyst metal is rhodium and when the ligand is Xantphos, the liquid reaction medium can contain about 0.01 mol % to 20 mol % rhodium and up to about 50 mol % Xantphos.

Examples of rhodium precursors include, but are not limited to, the following of rhodium at any suitable oxidative state (e.g., (I), (II), or (III)) and mixtures thereof: oxides; inorganic salts such as rhodium fluoride, rhodium chloride, rhodium bromide, rhodium iodide, and rhodium sulfate; rhodium salts of carboxylic acids such as rhodium acetate; di-rhodium tetraacetate, rhodium acetylacetonate, rhodium (II) isobutyrate, rhodium(II) 2-ethylhexanoate; rhodium carbonyl compounds such as $Rh_4(CO)_{12}$, $Rh_6(CO)_{16}$, (acetylacetonato)dicarbonylrhodium(I); and other common rhodium species such as chlorodicarbonylrhodium dimer, $[RhCOD(OMe)]_2$, $[Rh(CO)_2(acetylacetonato)]$, and the like.

If a catalyst support is used, the catalyst compound can be loaded onto the catalyst support in any amount, provided that the method proceeds to the desired products. For example, the catalyst compound can be loaded onto the support in an amount that is greater than about 0.01 wt % of the group 9 metal, such as greater than about 0.05 wt % of the group 9 metal, based on the total weight of the catalyst compound plus support. For example, the catalyst compound can be loaded onto the support in an amount that is less than about 20 wt % of the group 9 metal, such as less than about 10 wt % of the group 9 metal, based on the total weight of the catalyst compound and support.

In at least one embodiment, a reaction mixture includes a loading of a catalyst $M[L]_n$ (where M is rhodium, L is any suitable ligand, such as phosphine, capable of coordinating a group 9 metal, and n is a positive integer, such as 1, 2, 3, 4, 5, or 6) that is about 10 mol % or less, relative to an olefin. In at least one embodiment, the loading of a catalyst $M[L]_n$ in a hydroformylation reaction is from about 0.0005 mol % to about 8 mol %, such as from about 0.001 mol % to about 4 mol %, such as from 0.005 mol % to about 2 mol %, such as from about 0.01 mol % to about 1.5 mol %, such as from about 0.02 mol % to about 1 mol %, such as from about 0.03 mol % to about 0.5 mol %.

In at least one embodiment, suitable transition metal complexes can include Rh-based complexes. Additionally, such transition metal complexes can be bridged by a bidentate ligand. Suitable bidentate ligands include, but are not limited to, bidentate phosphorus ligands, such as Xantphos.

Phosphine Compounds

The term "phosphine compound" refers to a phosphorous-containing organic compound having the formula $PR_3$, where each R is independently a hydrocarbyl group, such as an aryl group, an alkylaryl group, an alkyl group, or an aryl alkyl group, alternately each R group is the same.

Non-limiting examples of phosphines include $P(OMe)_3$, $P(OPh)_3$, triphenyl phosphine, tri-(n-butyl) phosphine, tri-(tert-butyl) phosphine, tri-(n-pentyl) phosphine, tri-(n-hexyl) phosphine, tri(n-heptyl) phosphine, tri-(n-octyl) phosphine, tri(n-nonyl) phosphine, tri-(n-decyl) phosphine, and any mixture of two or more thereof, and the like.

The term "alkylphosphite" is a subset of phosphite, wherein each R is independently an alkoxy group, alternately each R group is the same. Similarly, the term "arylphosphite" is a subset of phosphite, wherein each R is independently an aryloxy group, alternately each R group is the same. The term "diphosphite" when used without the "substituted" modifier refers to a compound of the formula $R_2$—when $u_2$, wherein each R is independently alkoxy, aryloxy, and aralkoxy, as those terms are defined above, and wherein L is alkoxydiyl or aryloxydiyl. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$.

In further embodiments, the rhodium complex is a $[RhCOD(OMe)]_2$ complex or variation thereof that is soluble in the reaction solvent and does not contain strong phosphine ligands. While not wishing to be bound by any particular theory, it is believed that phosphines are better sigma donors than phosphites and may enhance selectivity to the desired aldehyde of the catalyst system.

Products

Alkene Products

Processes of the present disclosure produce alkenes. An alkene can be represented by formula (IV):

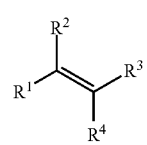

$$\tag{IV}$$

where each of $R^1$ and $R^2$ is independently hydrogen, alkoxide, or substituted or unsubstituted hydrocarbyl; and each of $R^3$ and $R^4$ is independently hydrogen, or substituted or unsubstituted hydrocarbyl. In at least one embodiment, each of $R^1$ and $R^2$ is hydrogen.

Oxygenates: Aldehyde Products

Processes of the present disclosure also produce aldehyde products (also known as oxygenates). In at least one embodiment, an aldehyde product is a $C_3$-$C_{41}$ aldehyde product represented by formula (V):

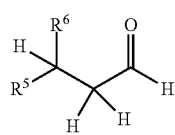

where each of $R^5$ and $R^6$ is independently hydrogen, or substituted or unsubstituted hydrocarbyl group, such as saturated hydrocarbyl group.

In at least one embodiment, each of $R^5$ and $R^6$ is independently hydrogen, or a substituted or unsubstituted hydrocarbyl group. In at least one embodiment, $R^5$ and $R^6$ are independently hydrogen or $C_1$ to $C_{38}$ alkyl, such as $C_1$ to $C_{20}$ alkyl, such as $C_1$ to $C_{10}$ alkyl, such as $C_1$ to $C_5$ alkyl. In at least one embodiment, one or more of $R^5$ and $R^6$ is $C_1$ to $C_{38}$ alkyl, such as $C_1$ to $C_{20}$ alkyl, such as $C_1$ to $C_{10}$ alkyl, such as $C_1$ to $C_5$ alkyl.

In at least one embodiment, one or more of $R^5$ and $R^6$ is $C_{10}$ to $C_{38}$ alkyl, such as $C_{20}$ to $C_{38}$ alkyl, such as $C_{30}$ to $C_{38}$ alkyl. In at least one embodiment, $R^5$ is hydrogen and $R^6$ is $C_{10}$ to $C_{38}$ alkyl, such as $C_{20}$ to $C_{38}$ alkyl, such as $C_{30}$ to $C_{38}$ alkyl.

Supports

In at least one embodiment, the catalyst compound utilized in a method of the present disclosure can be bound to or deposited on a solid catalyst support. The solid catalyst support will render the catalyst compound heterogeneous. The catalyst support can increase catalyst strength and attrition resistance. Catalyst supports include silicas, aluminas, silica-aluminas, aluminosilicates, including zeolites and other crystalline porous aluminosilicates, as well as titanias, zirconia, magnesium oxide, carbon, and cross-linked, reticular polymeric resins, such as functionalized cross-linked polystyrenes, e.g., chloromethyl-functionalized cross-linked polystyrenes. The catalyst compound can be deposited onto the support by any method known to those skilled in the art, including, for example, impregnation, ion-exchange, deposition-precipitation, and vapor deposition. Alternatively, the catalyst compound can be chemically bound to the support via one or more covalent chemical bonds, for example, the catalyst compound can be immobilized by one or more covalent bonds with one or more of substituents of the ligands of the catalyst.

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any suitable manner, such as a non-coordinating anion. For example, a non-coordinating anion can be a benzoic acid or a hindered carboxylate. Examples include aryl carboxylates, such as 3,5-dimethylbenzoate, and alkyl carboxylates, such as stearate or hexanoate or naphthenate.

Hydroformylation Conditions

In at least one embodiment, a method for preparing aldehydes includes contacting a $C_x$ aldehyde, a $C_y$ olefin, and a metal catalyst in a reaction vessel, wherein x is an integer of from 3 to 41 and y is an integer of from 2 to 40. The method includes obtaining a $C_{y+1}$ aldehyde product and a $C_{x-1}$ alkene product.

A temperature of the reaction mixture during hydroformylation can be maintained at any suitable temperature using a standard heating and/or cooling device. Reaction temperatures can range from about 0° C. to about 120° C., such as from about 10° C. to about 90° C., such as from about 25° C. to about 75° C., for example room temperature (e.g., 23° C., unless otherwise noted), optionally from 25° C. to 70° C., alternately from 30° C. to 65° C. Optionally the temperature of reaction is less than 70° C. Preferably the reaction maintains a reaction temperature of from 80° C. to 100° C. A reaction can be performed (e.g., stirring and/or heating of the reaction mixture) for any suitable amount of time, for example, until completion of the reaction. In at least one embodiment of the present disclosure, the reaction temperature is about 90° C. In at least one embodiment, a reaction time is from about 5 hours to about 100 hours, such as from about 15 hours to about 75 hours, such as about 24 hours or about 96 hours. A reaction pressure can be 150 psig or less.

The identity of the inert solvent which can be used in the reaction system is flexible so long as it is miscible with the catalyst system and with the reactants and reaction products, low in volatility so as to facilitate stripping reaction product and by-products from it, and, of course, either chemically inert in the hydroformylation reaction system or else forming in that system a derivative which is itself inert. Molecular weight can be factor in the reaction solvents as it relates to volatility, relatively high molecular weight being desired, of course, to facilitate retention of the inert solvent as a heavy end while the reaction products are stripped out of it.

Solvents include any suitable organic solvent that is inert under the hydroformylation conditions. Solvents include aromatic hydrocarbons, chlorinated hydrocarbons, ethers, aliphatic hydrocarbons, alcohols, or mixtures thereof. Suitable solvents include THF, acetone, dimethylformamide (DMF), pentane, isohexane, hexane, octane, benzene, xylene, toluene, methylcyclohexane, fluorobenzene, diethylether, dichloromethane, chloroform, and dimethyl sulfoxide (DMSO). In at least one embodiment of the present disclosure, the solvent is THF.

Alternatively, the hydroformylation is performed 'neat', e.g. without the presence of a solvent in a reaction mixture. In such embodiments, the reaction mixture includes only catalyst, aldehyde and olefin. The aldehyde and olefin can be diluent for the catalyst and the product.

In at least one embodiment, the conversion of feed material is about 50 mol % or greater, such as about 60 mol % or greater, such as about 70 mol % or greater, such as about 80 mol % or greater, such as about 95 mol % or greater, such as about 99% or greater.

In at least one embodiment, the hydroformylation reaction can occur under near or ambient pressure (atmospheric pressure), such as from about 28 inHg (13.7 psi, 94.8 KPa) to about 31 inHg (15.2 psi, 105 KPa), such as from about 29 inHg (14.2 psi) to about 30 inHg (14.7 psi).

The liquid reaction medium or catalyst solution which is employed includes, (a) the catalyst complex, (b) an excess of the organic ligand employed in forming the complex over and above the amount to complex the metallic component of the catalyst, (c) the hydroformylation reaction product along with by-products resulting from undesired condensation of the hydroformylation product aldehyde with itself, (d) a quantity of the olefin being hydroformylated, in an amount varying with the molecular weight of said olefin (the proportion of liquid olefin in the reaction medium usually being greater with high molecular weight olefins than with lower alkenes such as ethylene), and (e) in most systems involving the processing of olefins of low to moderate molecular weight, an inert reaction solvent. With higher weight olefins such as, for example, octene, the olefin itself in liquid phase can function as reaction solvent.

In at least one embodiment, a sterically encumbered acid, such as 3,5-dimethylbenzoic acid, can be used in order to reduce or prevent coordination of the benzoate to the rhodium catalyst. Without wishing to be bound by theory, it is thought that the acid functions as a non-coordinating anion.

It is a particular advantage of this method that it can be operated in the absence of syngas, e.g. the method is free of introducing syngas into the reaction vessel.

It is a particular advantage of this method that it can be operated in the absence of carbon monoxide, e.g. the method is free of introducing carbon monoxide into the reaction vessel.

It is a particular advantage of this method that it can be operated in the absence of syngas and carbon monoxide, e.g. the method is free of introducing syngas and carbon monoxide into the reaction vessel.

This invention also relates to:
1. A method for preparing aldehydes, comprising: contacting a $C_x$ aldehyde, a $C_y$ olefin, and a metal catalyst in a reaction vessel, wherein x is an integer of from 3 to 41 and y is an integer of from 2 to 40; and obtaining a $C_{y+1}$ aldehyde product and a $C_{x-1}$ alkene product.
2. The method of paragraph 1, wherein the olefin is an alpha olefin.
3. The method of paragraphs 1 or 2, further comprising maintaining a reaction temperature of from 80° C. to 100° C.
4. The method of any of paragraphs 1 to 3, further comprising maintaining a reaction pressure of 150 psig or less.
5. The method of any of paragraphs 1 to 4, wherein the method is free of introducing syngas into the reaction vessel.
6. The method of any of paragraphs 1 to 5, wherein the method is free of introducing carbon monoxide into the reaction vessel.
7. The method of any of paragraphs 1 to 6, wherein the alkene product is ethylene.
8. The method any of paragraphs 1 to 7, wherein the aldehyde is represented by formula (I):

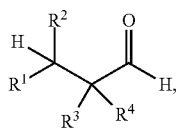

(I)

wherein each of $R^1$ and $R^2$ is independently hydrogen, alkoxide, or substituted or unsubstituted hydrocarbyl, and each of $R^3$ and $R^4$ is independently hydrogen, or substituted or unsubstituted hydrocarbyl.
9. The method of paragraph 8, wherein $R^1$ and $R^2$ are hydrogen.
10. The method of paragraphs 8 or 9, wherein $R^3$ and $R^4$ is independently hydrogen or $C_1$ to $C_5$ alkyl.
11. The method of any of paragraphs 8 to 10, wherein each of $R^3$ and $R^4$ is hydrogen.

12. The method of any of claims 1 to 11, wherein the $C_2$-$C_{40}$ olefin is represented by formula (II):

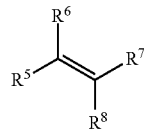

(II)

where each of $R^5$, $R^6$, $R^7$, and $R^8$ is independently hydrogen, or substituted or unsubstituted hydrocarbyl group.
13. The method of any of paragraphs 1 to 12, wherein the metal catalyst is represented by formula (III):

$$M[L]_n \qquad (III)$$

wherein M is a group 9 metal, L is any suitable ligand capable of coordinating a group 9 metal, and n is an integer of from 1 to 10.
14. The method of paragraph 13, wherein M is Rh or Co.
15. The method of paragraph 14, wherein the metal catalyst is selected from $Rh_4(CO)_{12}$, $Rh_6(CO)_{16}$, (acetylacetonato)dicarbonylrhodium(I), chlorodicarbonylrhodium dimer, chlorobis(ethylene)rhodium dimer, $HRh(CO)_4$, $HRh(CO)PPh_3$, and $[RhCOD(OMe)]_2$, $[Rh(CO)_2(acetylacetonato)]$.
16. The method of paragraph 14, wherein the metal catalyst is selected from $Co(acac)_3$, $HCo(CO)_4$, and $HRh(CO)(PPh_3)_3$.
17. The method of any of paragraphs 1 to 16, wherein the alkene product is represented by formula (IV):

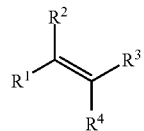

(IV)

wherein each of $R^1$ and $R^2$ is independently hydrogen, alkoxide, or substituted or unsubstituted hydrocarbyl; and each of $R^3$ and $R^4$ is independently hydrogen, or substituted or unsubstituted hydrocarbyl.
18. The method of paragraph 17, wherein $R^1$ and $R^2$ of formula (IV) is hydrogen.
19. The method of any of paragraphs 1 to 18, wherein the aldehyde product is represented by formula (V):

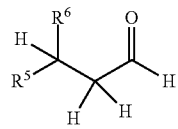

(V)

wherein each of $R^5$ and $R^6$ is independently hydrogen, or a substituted or unsubstituted hydrocarbyl group.
20. The method of paragraph 19, wherein at least one of $R^5$ and $R^6$ is $C_1$ to $C_{38}$ alkyl.
21. The method of paragraph 20, wherein at least one of $R^5$ and $R^6$ is $C_1$ to $C_{10}$ alkyl.
22. The method of paragraph 21, wherein at least one of $R^5$ and $R^6$ is $C_1$ to $C_5$ alkyl.
23. The method of paragraph 19, wherein at least one of $R^5$ and $R^6$ is $C_{10}$ to $C_{38}$ alkyl.

24. The method of paragraph 23, wherein at least one of $R^5$ and $R^6$ is $C_{20}$ to $C_{38}$ alkyl.

25. The method of paragraph 24, wherein at least one of $R^5$ and $R^6$ is $C_{30}$ to $C_{38}$ alkyl.

26. The method of paragraph 19, wherein $R^5$ is hydrogen and $R^6$ is $C_{10}$ to $C_{38}$ alkyl.

27. The method of paragraph 26, wherein $R^6$ is $C_{30}$ to $C_{38}$ alkyl.

28. The method of paragraph 1, wherein the aldehyde is propanal and the aldehyde product is heptanal.

29. The method of paragraph 1, wherein the aldehyde is propanal and the aldehyde product is norbornal.

30. The method of paragraph 1, wherein the aldehyde is propanal and the aldehyde product is a tridecanal.

31. A method for preparing aldehydes, comprising:

1) contacting:

a) a $C_x$ aldehyde, where x is an integer of from 3 to 41, represented by formula (I):

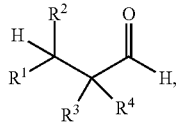

(I)

wherein each of $R^1$ and $R^2$ is independently hydrogen, alkoxide, or substituted or unsubstituted hydrocarbyl, and each of $R^3$ and $R^4$ is independently hydrogen, or substituted or unsubstituted hydrocarbyl;

b) a $C_y$ alpha olefin, where y is an integer of from 2 to 40, represented by formula (II):

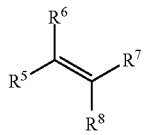

(II)

where each of $R^5$, $R^6$, $R^7$, and $R^8$ is independently hydrogen, or substituted or unsubstituted hydrocarbyl group; and c) a metal catalyst represented by formula (III): $M[L]_n$ (III)

wherein M is a group 9 metal, preferably Rh or Co, L is any suitable ligand capable of coordinating a group 9 metal, and n is an integer of from 1 to 10;

in a reaction vessel at a reaction temperature of from 80° C. to 100° C. and a reaction pressure of 150 psig or less; and 2) obtaining:

i) a $C_{y+1}$ aldehyde product represented by formula (V):

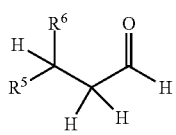

(V)

wherein each of $R^5$ and $R^6$ is as defined above; and ii) a $C_{x-1}$ alkene product represented by formula (IV):

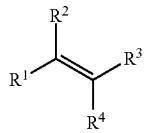

(IV)

wherein each of $R^1$, $R^2$, $R^3$ and $R^4$ is as defined above, where, optionally, the method is free of introducing syngas and or carbon monoxide into the reaction vessel.

32. The method of paragraph 31, wherein the alkene product is ethylene.

33. The method of paragraph 31, wherein each $R^1$ and $R^2$ is hydrogen, each $R^3$ and $R^4$ is independently hydrogen or $C_1$ to $C_5$ alkyl, each $R^5$ and $R^6$ is $C_1$ to $C_5$ alkyl, and M is Rh or Co.

35. The method of paragraph 31, wherein the metal catalyst is selected from $Rh_4(CO)_{12}$, $Rh_6(CO)_{16}$, (acetylacetonato) dicarbonylrhodium(I), chlorodicarbonylrhodium dimer, chlorobis(ethyl ene)rhodium dimer, $HRh(CO)_4$, $HRh(CO)PPh_3$, $[RhCOD(OMe)]_2$, $[Rh(CO)_2(acetylacetonato)]$, $Co(acac)_3$, $HCo(CO)_4$, and $HRh(CO)(PPh_3)_3$.

35. The method of paragraph 31, wherein the aldehyde is propanal and the aldehyde product is heptanal, norbornal, tridecanal, or a mixture thereof.

EXPERIMENTAL

All reactions were carried out under an inert atmosphere. Anhydrous solvents were purchased from commercial sources and were degassed and dried over molecular sieves prior to use. Deuterated solvents were purchased from commercial sources, degassed and dried over molecular sieves prior to use. Norbornene, propanal, heptanal, 3,5-dimethylbenzoic acid, Xantphos, and $[RhCOD(OMe)]_2$ were purchased from commercial sources and used as received. Hexene(s), octene(s), and dodecene(s) were obtained from refinery feedstock and degassed and dried with Na/K.

All $^1H$ NMR data were collected on a Bruker AVANCE III 400 MHz spectrometer running Topspin™ 3.0 software at room temperature (RT) using a deuterated solvent for all materials.

GC-MS analysis: yields of hydroformylation product and catalyst turnover numbers were calculated from data recorded on an Agilent™ 6890 GC spectrometer as described below. Conversion was determined using $^1H$ NMR or GC-MS by relative integration of: area product/ (area starting material+area product).

All reactions were carried out under an inert atmosphere at 90° C. with THF as solvent. Experimental validation was obtained using propanal as a donor aldehyde in combination with a variety of acceptor olefins such as 1-hexene, as well as commercial $C_6$ (linear), $C_8$ (mixed) and $C_{12}$ (linear) feeds. A 20-fold excess of propanal was used with a comparatively high catalyst loading in an effort to enhance conversion values. Propanal is comparatively inexpensive and the ethylene by-product formed during the transfer hydroformylation process is volatile, hence easily separable. Furthermore, the ability to evolve ethylene gas provides an alternative method to drive transfer hydroformylation reactions to high conversion. In an industrial process, continuous ethylene removal in the vapor phase can be used to enhance conversion values. Table 1 illustrates the results obtained under the above described conditions. Experiments were conducted under an inert atmosphere at 90° C. with THF as solvent. Catalyst loading was based on [RhCOD(OMe)]$_2$. Two equivalents of 3,5-dimethylbenzoic acid and Xantphos were used for every equivalent of [RhCOD(OMe)]$_2$. All the mol % values were calculated based on the theoretical molecular weight of the acceptor olefin. Entry 5 represents the conditions of which the feed contained a highly complex mixture of $C_8$ isomers. Definitive evidence for transfer hydroformylation using propanal as the formyl source was obtained for linear $C_6$ (entry 3) and $C_{12}$ olefins (entry 6). Conversion values were low for a $C_8$ rich $C_7$-$C_9$ feed containing large quantities of internal olefins. Trace evidence for the presence of a variety of $C_9$ oxygenates was detected in GC-MS analysis (entry 5). Without wishing to be bound by theory, it is thought that the high degree of branching internal olefins interferes with the ability or the rate of transfer hydroformylation using the Rh-Xantphos system. The 1,5-cyclooctadiene (COD) precursor was found to undergo isomerization to afford 1,3 and 1,4 cyclooctadienes. In all experiments utilizing propanal the concentration of ethylene (based on GC integration) was found to be higher than the desired transfer OXO products. This finding is consistent with decarbonylation to syngas as a competing reaction pathway. A process may benefit from the presence of low partial pressures of syngas.

TABLE 1

| Entry | Donor Aldehyde (Equivalent) | Donor Aldehyde | Acceptor Olefin | Reaction Time | Catalyst Loading (mol %) |
|---|---|---|---|---|---|
| 1 | 2 | heptanal | norbornene | 24 h | 1 |
| 2 | 2 | propanal | norbornene | 24 h | 1 |
| 3 | 20 | propanal | 1-hexene | 24 h | 1 |
| 4 | 20 | propanal | hexenes | 96 h | 10 |
| 5 | 20 | propanal | octenes | 96 h | 10 |
| 6 | 20 | propanal | dodecenes | 96 h | 10 |

| Entry | Detected Product(s) | Conversion |
|---|---|---|
| 1 | norbornal | 97-99% |
| 2 | norbornal | 30-50% |
| 3 | heptanal | 2% |
| 4 | heptanal | 17% |
| 5 | $C_9$ oxygenates | <1% |
| 6 | tridecanals | 8% |

Overall, aldehydes, catalysts, catalyst systems, and processes of the present disclosure can provide oxygenates from olefins. Hydroformylations can be a transfer hydroformylation including forming oxygenates from olefins which includes a hydroformylation reaction of aldehydes as a formyl source alternative to syngas. The present transfer hydroformylation process can be performed at low-temperature and at or near ambient pressure for the conversion of higher olefins into higher aldehydes, thus reducing the formation of by-products such as via double bond or skeletal isomerization of the feedstock; or via further conversion of the formed aldehydes and alcohols (i.e., formation of condensation products; decarbonylation; further oxidation). The use of gaseous olefinic products (e.g., ethylene) instead of strained olefins (e.g., norbornene) improves the control equilibria in transfer hydroformylation reactions. The present disclosure demonstrates that transfer hydroformylation can be used on higher olefins when, for example, propionaldehyde (propanal) is utilized as feedstock, leading to the formation of oxygenates.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

The invention claimed is:

1. A method for preparing aldehydes, comprising:
contacting a $C_x$ aldehyde, a $C_y$ olefin, and a metal catalyst in a reaction vessel while maintaining a reaction temperature of 120° C. or less and a pressure of 150 psig or less, wherein x is an integer of from 3 to 41 and y is an integer of from 2 to 40; and
obtaining a $C_{y+1}$ aldehyde product and a $C_{x-1}$ alkene product,
wherein the $C_y$ olefin is a linear alpha olefin.

2. The method of claim 1, wherein the alkene product consists essentially of linear alkenes.

3. The method of claim 1, wherein the reaction temperature is from 80° C. to 100° C.

4. The method of claim 1, wherein the reaction pressure is at or near ambient pressure.

5. The method of claim 1, wherein the method is free of introducing syngas into the reaction vessel.

6. The method of claim 1, wherein the method is free of introducing carbon monoxide into the reaction vessel.

7. The method of claim 1, wherein the alkene product is ethylene.

8. The method of claim 1, wherein the aldehyde is represented by formula (I):

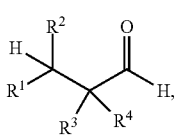

(I)

wherein each of $R^1$ and $R^2$ is independently hydrogen, alkoxide, or substituted or unsubstituted hydrocarbyl, and each of $R^3$ and $R^4$ is independently hydrogen, or substituted or unsubstituted hydrocarbyl.

9. The method of claim 8, wherein $R^1$ and $R^2$ are hydrogen.

10. The method of claim 8, wherein $R^3$ and $R^4$ is independently hydrogen or $C_1$ to $C_5$ alkyl.

11. The method of claim 8, wherein each of $R^3$ and $R^4$ is hydrogen.

12. The method of claim 1, wherein the $C_2$-$C_{40}$ olefin is represented by formula (II):

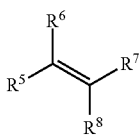

(II)

where each of $R^5$, $R^6$, $R^7$, and $R^8$ is independently hydrogen, or substituted or unsubstituted hydrocarbyl group.

13. The method of claim 1, wherein the metal catalyst is represented by formula (III):

$$M[L]_nX \qquad (III)$$

wherein M is a group 9 metal, L is any suitable ligand capable of coordinating a group 9 metal, and n is an integer of from 1 to 10.

14. The method of claim 13, wherein M is Rh or Co.

15. The method of claim 14, wherein the metal catalyst is selected from $Rh_4(CO)_{12}$, $Rh_6(CO)_{16}$, (acetylacetonato)dicarbonylrhodium(I), chlorodicarbonylrhodium dimer, chlorobis(ethylene)rhodium dimer, $HRh(CO)_4$, $HRh(CO)PPh_3$, $[RhCOD(OMe)]_2$, $[Rh(CO)_2(acetylacetonato)]$.

16. The method of claim 14, wherein the metal catalyst is selected from $Co(acac)_3$, $HCo(CO)_4$, and $HRh(CO)(PPh_3)_3$.

17. The method of claim 1, wherein the alkene product is represented by formula (IV):

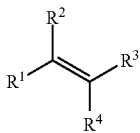

(IV)

wherein each of $R^1$ and $R^2$ is independently hydrogen, alkoxide, or substituted or unsubstituted hydrocarbyl; and each of $R^3$ and $R^4$ is independently hydrogen, or substituted or unsubstituted hydrocarbyl.

18. The method of claim 17, wherein $R^1$ and $R^2$ of formula (IV) is hydrogen.

19. The method of claim 1, wherein the aldehyde product is represented by formula (V):

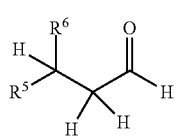

(V)

wherein each of $R^5$ and $R^6$ is independently hydrogen, or a substituted or unsubstituted hydrocarbyl group.

20. The method of claim 19, wherein at least one of $R^5$ and $R^6$ is $C_1$ to $C_{38}$ alkyl.

21. The method of claim 20, wherein at least one of $R^5$ and $R^6$ is $C_1$ to $C_{10}$ alkyl.

22. The method of claim 21, wherein at least one of $R^5$ and $R^6$ is $C_1$ to $C_5$ alkyl.

23. The method of claim 19, wherein at least one of $R^5$ and $R^6$ is $C_{10}$ to $C_{38}$ alkyl.

24. The method of claim 23, wherein at least one of $R^5$ and $R^6$ is $C_{20}$ to $C_{38}$ alkyl.

25. The method of claim 24, wherein at least one of $R^5$ and $R^6$ is $C_{30}$ to $C_{38}$ alkyl.

26. The method of claim 19, wherein $R^5$ is hydrogen and $R^6$ is $C_{10}$ to $C_{38}$ alkyl.

27. The method of claim 26, wherein $R^6$ is $C_{30}$ to $C_{38}$ alkyl.

28. The method of claim 1, wherein the aldehyde is propanal and the aldehyde product is heptanal.

29. The method of claim 1, wherein the aldehyde is propanal and the aldehyde product is norbornal.

30. The method of claim 1, wherein the aldehyde is propanal and the aldehyde product is a tridecanal.

31. A method for preparing aldehydes, comprising:
1) contacting:
a) a $C_x$ aldehyde, where x is an integer of from 3 to 41, represented by formula (I):

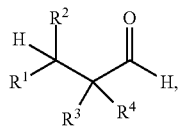

(I)

wherein each of $R^1$ and $R^2$ is independently hydrogen, alkoxide, or substituted or unsubstituted hydrocarbyl, and each of $R^3$ and $R^4$ is independently hydrogen, or substituted or unsubstituted hydrocarbyl;

b) a $C_y$ linear alpha olefin, where y is an integer of from 2 to 40, represented by formula (II):

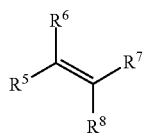

(II)

where each of $R^5$, $R^6$, $R^7$, and $R^8$ is independently hydrogen, or substituted or unsubstituted hydrocarbyl group; and c) a metal catalyst represented by formula (III): M[L]$_n$ (III)

wherein M is a group 9 metal, preferably Rh or Co, L is any suitable ligand capable of coordinating a group 9 metal, and n is an integer of from 1 to 10;

in a reaction vessel at a reaction temperature of from 80° C. to 100° C. and a reaction pressure of 150 psig or less; and 2) obtaining:

i) a $C_{y+1}$ aldehyde product represented by formula (V):

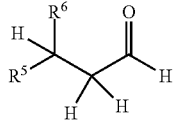

(V)

wherein each of $R^5$ and $R^6$ is as defined above; and ii) a $C_{x-1}$ alkene product represented by formula (IV):

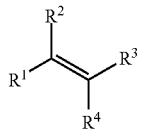

(IV)

wherein each of $R^1$, $R^2$, $R^3$ and $R^4$ is as defined above.

32. The method of claim 31, where the method is free of introducing syngas and or carbon monoxide into the reaction vessel.

33. The method of claim 31, wherein the alkene product is ethylene.

34. The method of claim 31, wherein each $R^1$ and $R^2$ is hydrogen, each $R^3$ and $R^4$ is independently hydrogen or $C_1$ to $C_5$ alkyl, each $R^5$ and $R^6$ is $C_1$ to $C_5$ alkyl, and M is Rh or Co.

35. The method of claim 31, wherein the metal catalyst is selected from $Rh_4(CO)_{12}$, $Rh_6(CO)_{16}$, (acetylacetonato)dicarbonylrhodium(I), chlorodicarbonylrhodium dimer, chlorobis(ethylene)rhodium dimer, $HRh(CO)_4$, $HRh(CO)PPh_3$, $[RhCOD(OMe)]_2$, $[Rh(CO)_2(acetylacetonato)]$, $Co(acac)_3$, $HCo(CO)_4$, and $HRh(CO)(PPh_3)_3$.

36. The method of claim 31, wherein the aldehyde is propanal and the aldehyde product is heptanal, norbornal, tridecanal, or a mixture thereof.

37. The method of claim 31, wherein the alkene product consists essentially of linear alkenes.

38. The method of claim 1, wherein the metal catalyst is selected from $Rh_4(CO)_{12}$, $Rh_6(CO)_{16}$, (acetylacetonato)dicarbonylrhodium(I), chlorodicarbonylrhodium dimer, chlorobis(ethylene)rhodium dimer, $HRh(CO)_4$, $HRh(CO)PPh_3$, $[RhCOD(OMe)]_2$, $[Rh(CO)_2(acetylacetonato)]$, $Co(acac)_3$, $HCo(CO)_4$, and $HRh(CO)(PPh_3)_3$.

* * * * *